US011565118B2

(12) United States Patent
Helgeson et al.

(10) Patent No.: US 11,565,118 B2
(45) Date of Patent: Jan. 31, 2023

(54) CIRCULAR CATHETER WITH NON-CIRCULAR SHAPING WIRE

(71) Applicant: St. Jude Medical, Cardiology Division, Inc., St. Paul, MN (US)

(72) Inventors: Zach Helgeson, Richfield, MN (US); Ryan Hendrickson, Albertville, MN (US); Brad Seibert, Saint Louis Park, MN (US); Neil Hawkinson, Ramsey, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 844 days.

(21) Appl. No.: 15/462,388

(22) Filed: Mar. 17, 2017

(65) Prior Publication Data

US 2017/0274177 A1    Sep. 28, 2017

Related U.S. Application Data

(60) Provisional application No. 62/312,181, filed on Mar. 23, 2016.

(51) Int. Cl.
 *A61B 18/14*    (2006.01)
 *A61N 1/362*    (2006.01)
 (Continued)

(52) U.S. Cl.
 CPC .............. *A61N 1/362* (2013.01); *A61B 5/283* (2021.01); *A61B 5/6852* (2013.01);
 (Continued)

(58) Field of Classification Search
 CPC ...... A61N 1/362; A61B 5/042; A61B 5/6869; A61B 18/1492; A61B 2018/00351; A61B 2018/00839; A61B 2018/1407; A61B 2018/1467; A61B 5/283; A61B 5/6852; A61M 25/0009; A61M 25/0147; A61M 25/0136
 See application file for complete search history.

(56) References Cited

U.S. PATENT DOCUMENTS 6,254,568 B1 *  7/2001  Ponzi ................ A61M 25/0144
                                                                    604/95.04
7,606,609 B2    10/2009  Muranushi et al.
(Continued)

*Primary Examiner* — Eun Hwa Kim
*Assistant Examiner* — Catherine Premraj
(74) *Attorney, Agent, or Firm* — Wiley Rein LLP

(57) ABSTRACT

A catheter has a body including a proximal region, a neck region, and a distal region. A shaping wire is disposed within the distal region to predispose it into at least a partial loop, which may have a fixed or variable radius of curvature. The shaping wire includes a distal portion having a circular transverse cross-sectional shape and a proximal portion having a non-circular (e.g., rectangular) transverse cross-sectional shape. The proximal portion of the shaping wire can have a width-to-thickness ratio of at least about 4, such as about 4.67. A transition portion can promote a gradual transition from the circular to the non-circular transverse cross-sectional shape, for example by increasing a width of the shaping wire by about 0.001" and/or by decreasing a thickness of the shaping wire by about 0.001" for every about 0.004" in length through the transition portion.

13 Claims, 3 Drawing Sheets

(51) Int. Cl.
*A61B 5/00* (2006.01)
*A61M 25/00* (2006.01)
*A61M 25/01* (2006.01)
*A61B 5/283* (2021.01)
*A61B 18/00* (2006.01)

(52) U.S. Cl.
CPC ..... *A61B 18/1492* (2013.01); *A61M 25/0009* (2013.01); *A61M 25/0147* (2013.01); *A61B 5/6869* (2013.01); *A61B 2018/00351* (2013.01); *A61B 2018/00839* (2013.01); *A61B 2018/1407* (2013.01); *A61B 2018/1467* (2013.01); *A61M 25/0136* (2013.01)

(56) References Cited

U.S. PATENT DOCUMENTS

| | | | |
|---|---|---|---|
| 8,369,923 B2 | 2/2013 | de la Rama et al. | |
| 2004/0193239 A1* | 9/2004 | Falwell | A61B 18/1492 607/122 |
| 2011/0257499 A1* | 10/2011 | de la Rama | A61B 5/0422 600/373 |
| 2012/0296366 A1* | 11/2012 | Rundquist | A61M 25/005 606/192 |
| 2013/0304047 A1* | 11/2013 | Grunewald | A61M 25/09 606/14 |

\* cited by examiner

CIRCULAR CATHETER WITH NON-CIRCULAR SHAPING WIRE

CROSS-REFERENCE TO RELATED APPLICATIONS

This application claims the benefit of U.S. provisional application No. 62/312,181, filed 23 Mar. 2016, which is hereby incorporated by reference as though fully set forth herein.

BACKGROUND

The instant disclosure relates to catheters for use in medical procedures, such as electrophysiology studies. In particular, the instant disclosure relates to a catheter for use in diagnostic and therapeutic procedures at or near an annular region of a patient's anatomy, such as the ostium of a pulmonary vein.

Catheters are used for an ever-growing number of procedures, such as diagnostic, therapeutic, and ablative procedures, to name just a few examples. Typically, the catheter is manipulated through the patient's vasculature and to the intended site, for example, a site within the patient's heart.

A typical electrophysiology catheter includes an elongate shaft and one or more electrodes on the distal end of the shaft. The electrodes may be used for ablation, diagnosis, or the like. Oftentimes, these electrodes are ring electrodes that extend about the entire circumference of the catheter shaft.

One specific use of an electrophysiology catheter is to map the atrial regions of the heart, and in particular the pulmonary veins, which are often origination points or foci of atrial fibrillation. Such electrophysiology mapping catheters typically have at least a partial loop shape at their distal end, oriented in a plane generally orthogonal to the longitudinal axis of the catheter shaft, which allows the loop to surround the pulmonary vein ostia.

Because of varying patient anatomies, however, it may be challenging to place the looped section of the catheter precisely in the pulmonary vein ostia. Torque strength and the ability to effectively rotate the loop section are important to accomplish this objective.

BRIEF SUMMARY

Disclosed herein is a catheter including: a catheter body having a proximal region, a neck region, and a distal region; and a shaping wire within the distal region to predispose the distal region into at least a partial loop, wherein the shaping wire includes a distal portion having a circular transverse cross-sectional shape and a proximal portion having a non-circular transverse cross-sectional shape. The catheter can also include a heat shrink layer about the proximal portion of the shaping wire. The at least a partial loop of the distal region can be of fixed or variable radius of curvature.

According to aspects of the disclosure, the proximal portion of the shaping wire has a width-to-thickness ratio of at least about 4, such as about 4.67. In other aspects of the disclosure, the proximal portion of the shaping wire has a rectangular transverse cross-sectional shape.

It is contemplated that the non-circular transverse cross-sectional shape of the proximal portion of the shaping wire promotes 1:1 torque transfer from the proximal region of the catheter body to the distal region of the catheter body. It is also contemplated that the non-circular transverse cross-sectional shape of the proximal portion of the shaping wire increases bonding surface area by at least 50% relative to the circular transverse cross-sectional shape of the distal portion of the shaping wire.

The shaping wire can also include a transition portion between the distal portion and the proximal portion. The transition portion can promote a gradual transition from the circular transverse cross-sectional shape of the distal region to the non-circular transverse cross-sectional shape of the proximal portion. For example, according to aspects of the disclosure, a width of the shaping wire can increase by 0.001" for every 0.004" in length through the transition portion and/or a thickness of the shaping wire can decreased by 0.001" for every 0.004" in length through the transition portion.

According to another embodiment, a method of manufacturing a catheter includes: forming a catheter body having a proximal region, a neck region, and a distal region; and forming the distal region of the catheter body into at least a partial loop via the use of a shaping wire, the shaping wire including: a distal portion having a circular transverse cross-sectional shape; and a proximal portion having a non-circular transverse cross-sectional shape.

According to aspects of the disclosure, the proximal portion of the shaping wire has a width-to-thickness ratio of at least about 4, such as about 4.67, and can have a rectangular transverse cross-sectional shape.

The shaping wire can also include a transition portion between the distal portion and the proximal portion that promotes a gradual transition from the circular transverse cross-sectional shape of the distal region to the non-circular transverse cross-sectional shape of the proximal portion.

Optionally, at least the proximal portion of the shaping wire can be encased in a heat shrink layer.

Also disclosed herein is a shaping wire that promotes 1:1 torque transfer within an elongate body of a medical device, the shaping wire including: a distal portion having a circular transverse cross-sectional shape; a proximal portion having a non-circular transverse cross-sectional shape; and a transition portion between the distal portion and the proximal portion that promotes a gradual transition between the circular transverse cross-sectional shape of the distal portion and the non-circular transverse cross-sectional shape of the proximal portion. A heat shrink layer can be provided about the proximal portion of the shaping wire.

The foregoing and other aspects, features, details, utilities, and advantages of the present invention will be apparent from reading the following description and claims, and from reviewing the accompanying drawings.

DETAILED DESCRIPTION

For the sake of illustration, certain embodiments of the disclosure will be explained herein with reference to an electrophysiology catheter utilized in cardiac electrophysiology studies. It should be understood, however, that the present teachings may be applied to good advantage in other contexts as well.

Figure 1:
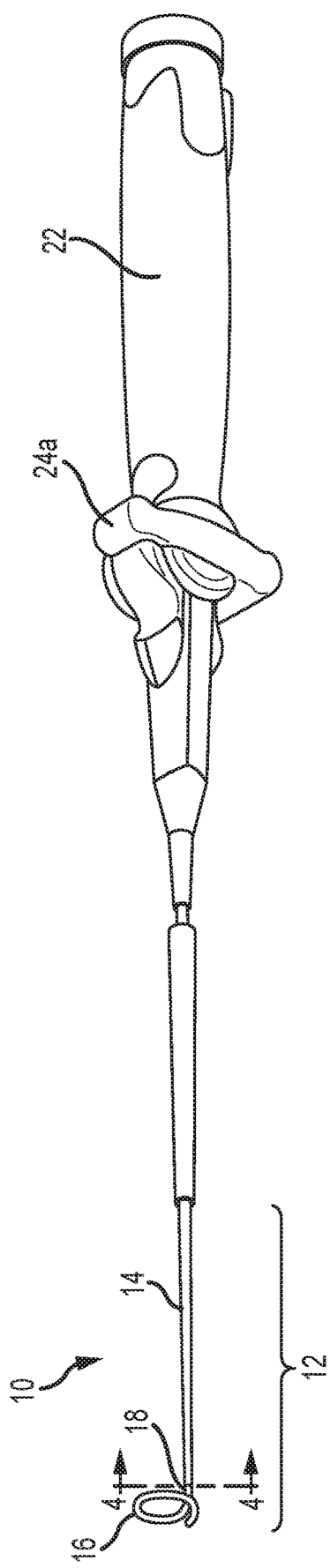
FIGS. 1 and 2 illustrate exemplary electrophysiology catheters.
Figure 2:
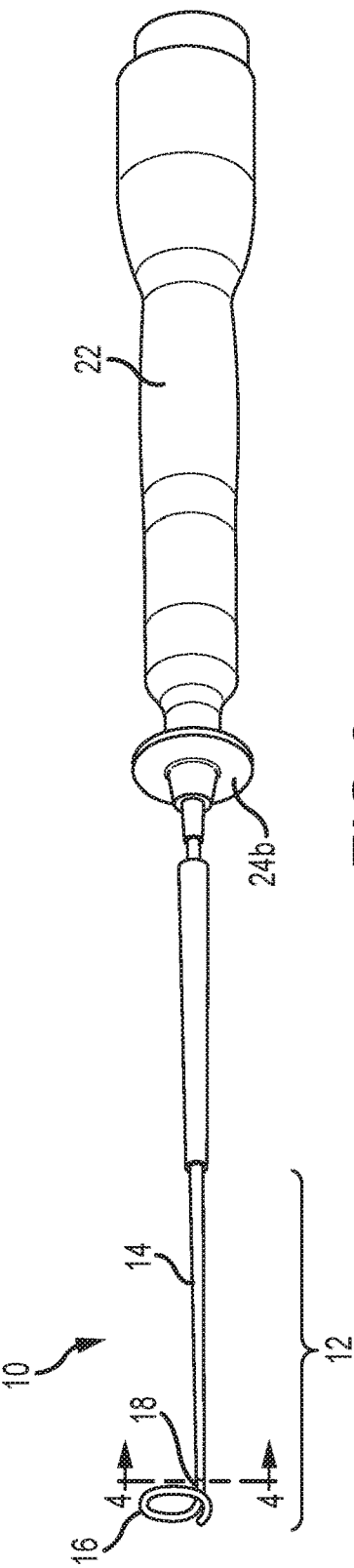

Referring now to the figures, FIGS. 1 and 2 depict two embodiments of an electrophysiology ("EP") catheter 10 according to aspects of the present disclosure. EP catheter 10 includes an elongate catheter body 12, which, in some embodiments, is tubular (e.g., it defines at least one lumen therethrough). Catheter body 12 includes a proximal region 14, a distal region 16, and a neck region 18 that offers a transition from proximal region 14 to distal region 16. In some embodiments, neck region 18 can include a coupling, such as described in U.S. provisional application No. 62/280,159, filed Jan. 19, 2016, which is hereby incorporated by reference as though fully set forth herein. The relative lengths of proximal region 14, distal region 16, and neck region 18 as depicted in FIGS. 1 and 2 are merely illustrative and may vary without departing from the spirit and scope of the instant disclosure. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 12 include, without limitation, polyamide-based thermoplastic elastomers (namely poly(ether-block-amide), such as PEBAX®), polyester-based thermoplastic elastomers (e.g., HYTREL®), thermoplastic polyurethanes (e.g., PELLETHANE®, ESTANE®), ionic thermoplastic elastomers, functionalized thermoplastic olefins, and any combinations thereof. In general, suitable materials for catheter body 12 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 may vary along its length. In general, the basic construction of catheter body 12 will be familiar to those of ordinary skill in the art, and thus will not be discussed in further detail herein except to the extent necessary to understand the instant disclosure.

Figure 3:
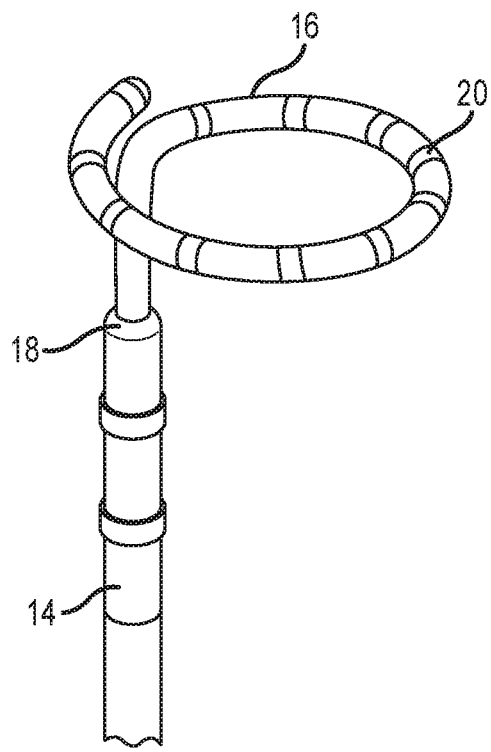
FIG. 3 is a close up of a portion of an electrophysiology catheter according to some embodiments of the instant disclosure.

As seen in FIG. 3, distal region 16 of catheter body 12 can be predisposed into at least a partial loop. This loop shape allows distal region 16 to conform to the shape, for example, of a pulmonary vein ostium. The partial loop may take a number of configurations, depending on the intended or desired use of EP catheter 10, consistent with the present teachings. Therefore, it should be understood that the loop configuration depicted in FIG. 3 is merely illustrative.

FIG. 3 also illustrates that distal region 16 can include a plurality of electrodes 20 disposed thereon. Electrodes 20 may be ring electrodes or any other electrodes suitable for a particular application of EP catheter 10. For example, where EP catheter 10 is intended for use in a contactless electrophysiology study, electrodes 20 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 may be employed for therapeutic purposes (e.g., cardiac ablation and/or pacing).

Referring again to FIGS. 1 and 2, a handle 22 is coupled to catheter body 12, for example at the proximal end of proximal region 14. Handle 22 can include suitable actuators (e.g., actuator 24a in FIG. 1; actuator 24b in FIG. 2) to control the deflection of catheter body 12, for example as described in U.S. Pat. No. 8,369,923, which is hereby incorporated by reference as though fully set forth herein. Various handles and their associated actuators for use in connection with electrophysiology catheters are known, and thus handle 22 will not be described in further detail herein.

Although in some embodiments the radius of curvature of the loop of distal region 16 may be fixed, it is also contemplated that it may be adjustable, for example to conform to the varying sizes of pulmonary vein ostia of patients of different ages. This additional control may be provided, for example, via the use of an activation wire 25, shown in FIG. 4, that is adapted to alter the radius of curvature of the loop of distal region 16. One suitable material for activation wire 25 is stainless steel, though other materials can be employed without departing from the spirit and scope of the instant disclosure.

In some embodiments, one end (e.g., the distal end) of activation wire 25 may be coupled to the tip of catheter body 12 (e.g., coupled to a distal-most tip electrode of electrodes 20), while the other end (e.g., the proximal end) of activation wire 25 may be coupled to an actuator (e.g., a thumb slider) on handle 22. Thus, for example, sliding the thumb slider proximally can place activation wire 25 in tension, thereby altering the radius of curvature of the loop of distal shaft 16.

Another exemplary mechanism for varying the radius of curvature of the loop of distal shaft 16 is described in U.S. Pat. No. 7,606,609, which is hereby incorporated by reference as though fully set forth herein.

Figure 4:
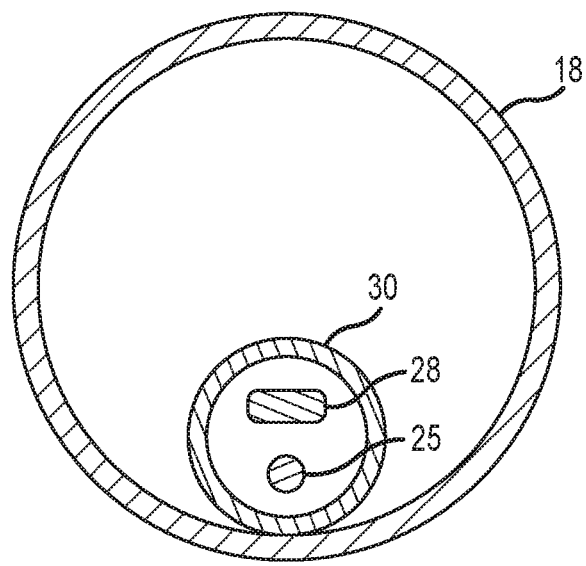
FIG. 4 is a transverse cross-section taken along line 4-4 in FIGS. 1 and 2.

FIG. 4 also depicts a shaping wire 28. Shaping wire 28 extends through neck region 18 and at least partially through distal region 16 in order to help predispose distal region 16 into the loop shape depicted throughout the Figures. Shaping wire 28 can be made from a shape memory material such as nitinol.

Figure 5:
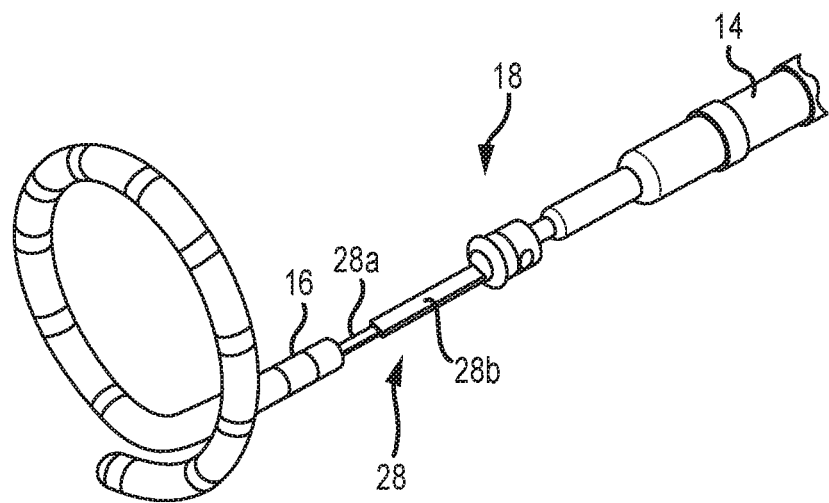
FIG. 5 is an exploded, close-up view depicting a shaping wire according to aspects of the instant disclosure.

FIG. 5 is an exploded view of proximal region 14, distal region 16, and neck region 18 that illustrates additional features of shaping wire 28 according to aspects of the instant disclosure. In particular, FIG. 5 shows that shaping wire 28 includes a distal portion 28a and a proximal portion 28b. While distal portion 28a of shaping wire 28 is generally circular, proximal section 28b of shaping wire 28 is non-circular.

The non-circular shape of proximal section 28b of shaping wire 28 offers several advantages. For example, it provides additional shear strength and bonding surface area relative to a circular shape. This increases the ability to transmit torque from proximal region 14 to distal region 16 (e.g., to re-orient the loop shape of distal region 16 as desired during a diagnostic or therapeutic procedure).

In embodiments of the disclosure, proximal section 28b of shaping wire 28 is flat. For example, the ratio of the width of proximal section 28b to the thickness of proximal section 28b can be at least about 4, such as about 4.67 (e.g., the width of proximal section 28b can be about 0.035 inches, and the thickness of proximal section 28b can be about 0.0075 inches). A proximal section 28b according to these exemplary dimensions offers more than a 50% increase in bonding surface area per unit length (more specifically, it offers about a 59% increase in bonding surface area per unit length), which in turn results in an increased bond tensile strength.

According to other embodiments of the disclosure, proximal section 28b has a different transverse cross-sectional shape, such as a square shape, a triangular shape, or any other non-circular shape.

According to aspects of the disclosure, proximal section 28b of shaping wire 28 is about 0.250 inches long.

Figure 6:
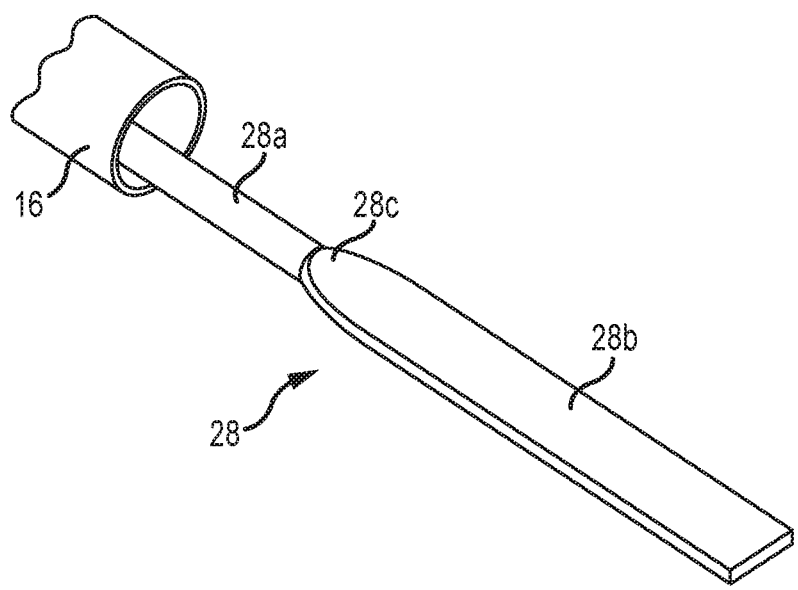
FIG. 6 is a close-up view of a shaping wire according to aspects of the instant disclosure.

As illustrated to good advantage in FIG. 6, it is contemplated that a transition region 28c between the round distal section 28a and the non-round (e.g., flat) proximal section 28b can be a gradual one. This has the advantageous effect of minimizing areas of stress concentration along shaping wire 28. Thus, for example, the width of shaping wire 28 can expand by about 0.001" while the thickness of shaping wire 28 can contract by about 0.001" for every 0.004" in length.

The flattened, non-circular profile of proximal section 28b of shaping wire 28, as well as transition region 28c, can be formed, for example, using a pneumatic press and stamping plates. It can also be formed using a direction action mechanical press, a toggle action mechanical press, a rolling mill, or the like.

Optionally, at least proximal section 28b of shaping wire 28 can be wrapped with a heat shrink layer 30 (shown in FIG. 4), such as a polyester (PET) heat shrink tubing. This imparts both electrical and mechanical isolation to proximal section 28b of shaping wire 28. That is, it protects nearby components from the flattened edges of proximal section 28b and also insulates proximal section 28b from electrical shorts.

In use, EP catheter 10 is introduced into a patient's body proximate an area of interest, such as a pulmonary vein ostium. Of course, EP catheter 10 may be introduced surgically (e.g., via an incision in the patient's chest) or non-surgically (e.g., navigated through the patient's vasculature to a desired site, with or without the assistance of a sheath, guidewire, or the like). The practitioner can then fine tune the positioning of the loop of distal region 16 relative to the patient's anatomy. The flattened, non-circular profile of proximal section 28b of shaping wire 28 will help transfer torque applied at handle 22 to distal region 16 at about a 1:1 ratio. Electrodes 20 may then be employed for diagnostic and/or therapeutic purposes.

Although several embodiments of this invention have been described above with a certain degree of particularity, those skilled in the art could make numerous alterations to the disclosed embodiments without departing from the spirit or scope of this invention.

It should also be understood that the dimensions of the embodiments described above are merely exemplary and can be varied without departing from the scope of the instant teachings. For example, in other embodiments, the ratio of the width of proximal section 28b to the thickness of proximal section 28b can be at least about 1.5; in still further embodiments, it can be at least about 2.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
   a catheter body having a proximal region, a neck region, and a distal region; and
   a shaping wire, including:
      a proximal portion having a proximal end, wherein the proximal end terminates within the neck region of the catheter body and wherein the proximal portion is bonded to the catheter body, and
      a distal portion disposed within the distal region of the catheter body to predispose the distal region of the catheter body into at least a partial loop,
   wherein the distal portion of the shaping wire has a circular transverse cross-sectional shape and the proximal portion of the shaping wire has a non-circular transverse cross-sectional shape defining a bonding surface area.

2. The catheter according to claim 1, wherein the proximal portion of the shaping wire has a width-to-thickness ratio of at least 4.

3. The catheter according to claim 2, wherein the width-to-thickness ratio is 4.67.

4. The catheter according to claim 1, wherein the proximal portion of the shaping wire has a rectangular transverse cross-sectional shape.

5. The catheter according to claim 1, further comprising a heat shrink layer about the proximal portion of the shaping wire.

6. The catheter according to claim 1, wherein the non-circular transverse cross-sectional shape of the proximal portion of the shaping wire promotes 1:1 torque transfer from the proximal region of the catheter body to the distal region of the catheter body.

7. The catheter according to claim 1, wherein the non-circular transverse cross-sectional shape of the proximal portion of the shaping wire increases the bonding surface area by at least 50% relative to the circular transverse cross-sectional shape of the distal portion of the shaping wire.

8. The catheter according to claim 1, wherein the shaping wire further includes a transition portion between the distal portion of the shaping wire and the proximal portion of the shaping wire, and wherein the transition portion promotes a gradual transition from the circular transverse cross-sectional shape of the distal region to the non-circular transverse cross-sectional shape of the proximal portion.

9. The catheter according to claim 8, wherein a width of the shaping wire increases by 0.001" for every 0.004" in length through the transition portion.

10. The catheter according to claim 8, wherein a thickness of the shaping wire decreases by 0.001" for every 0.004" in length through the transition portion.

11. The catheter according to claim 1, wherein the at least a partial loop of the distal region has a fixed radius of curvature.

12. The catheter according to claim 1, wherein the at least a partial loop of the distal region has a variable radius of curvature.

13. A catheter comprising:
   a catheter body having a proximal region coupled to a handle, a neck region, and a distal region; and an activation wire including a proximal end coupled to an actuator within the handle and a distal end coupled to the distal region of the catheter body, the activation wire configured to alter a radius of curvature of the distal region;

a shaping wire having a proximal end, wherein the proximal end of the shaping wire terminates within the neck region of the catheter body, and including a proximal portion disposed within the neck region of the catheter body and bonded to the catheter body, and a distal portion disposed within the distal region of the catheter body to predispose the distal region into at least a partial loop, wherein the distal portion of the shaping wire has a circular transverse cross-sectional shape and the proximal portion of the shaping wire has a non-circular transverse cross-sectional shape defining a bonding surface area.

\* \* \* \* \*